United States Patent [19]

Jones et al.

[11] 4,315,009

[45] Feb. 9, 1982

[54] ANTISECRETORY GUANIDINE DERIVATIVES AND PHARMACEUTICAL COMPOSITIONS CONTAINING THEM

[75] Inventors: Derrick F. Jones, Macclesfield; Keith Oldham, Cheadle, both of England

[73] Assignee: Imperial Chemical Industries Limited, London, England

[21] Appl. No.: 4,531

[22] Filed: Jan. 18, 1979

[30] Foreign Application Priority Data

Jan. 18, 1978 [GB] United Kingdom .............. 1992/78

[51] Int. Cl.³ ............................................ C07D 277/20
[52] U.S. Cl. ................................ 424/248.4; 424/263; 424/269; 424/270; 424/272; 424/273 R; 548/143; 548/193; 548/233
[58] Field of Search ............... 260/306.8 R; 548/193, 548/143, 233; 424/268, 269, 248.4, 263, 270, 272, 273 R

[56] References Cited

U.S. PATENT DOCUMENTS

| | | | |
|---|---|---|---|
| 4,088,769 | 5/1978 | Black et al. | 424/270 |
| 4,089,965 | 5/1978 | Angier et al. | 424/270 |
| 4,154,844 | 5/1979 | Durant et al. | 424/270 |
| 4,160,030 | 7/1979 | Durant et al. | 424/270 |
| 4,165,378 | 4/1979 | Gilman et al. | 424/270 |

FOREIGN PATENT DOCUMENTS

| | | |
|---|---|---|
| 842346 | 6/1952 | Fed. Rep. of Germany . |
| 955684 | 1/1957 | Fed. Rep. of Germany . |
| 2817078 | 11/1978 | Fed. Rep. of Germany . |
| 1351391 | 12/1963 | France . |
| 7811536 | 4/1978 | France . |
| 53-141271 | 12/1978 | Japan . |
| 1185139 | 3/1970 | United Kingdom . |
| 1305546 | 2/1973 | United Kingdom . |
| 1305549 | 2/1973 | United Kingdom . |
| 1338169 | 11/1973 | United Kingdom . |
| 1351025 | 4/1974 | United Kingdom . |
| 1397436 | 6/1975 | United Kingdom . |
| 1421999 | 1/1976 | United Kingdom . |

*Primary Examiner*—Nicholas S. Rizzo
*Attorney, Agent, or Firm*—Cushman, Darby & Cushman

[57] ABSTRACT

The guanidine derivative has the formula:

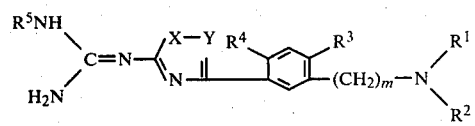

where X is O or S: Y is N, CH or CCH$_3$: m is 0 or 1: $R^1$ is hydrogen and $R^2$ cyano, trifluoroacetyl, C$_{1-6}$ alkanoyl, 4,5-dihydro-4-oxothiazol-2-yl or A-B where A is 3,4-dioxocyclobutene-1,2-diyl or C=Z where Z is oxygen, sulphur, NCN, NNO$_2$, CHNO$_2$, NCONH$_2$, C(CN)$_2$, NCOR$^6$, NCO$_2$R$^6$, NSO$_2$R$^6$ or NR$^7$ where R$^6$ is C$_{1-6}$alkyl and R$^7$ is hydrogen or C$_{1-6}$alkyl and B is C$_{1-6}$alkyl, alkoxy or alkylthio or NR$^8$R$^9$ where R$^8$ and R$^9$ are hydrogen, C$_{1-10}$alkyl, C$_{3-10}$alkenyl, alkynyl or alkoxyalkyl, C$_{2-6}$ (primary hydroxy)alkyl, or, when R$^9$ is hydrogen, R$^8$ is 2-[[5-dimethylaminomethylfuran-2-yl]methylthio]-ethylamino or R$^8$ and R$^9$ are together a 5- or 6-membered non-aromatic ring optionally containing an additional N or O; or $R^1$ and $R^2$ are together imidazolidin-2-ylidene: $R^3$ is hydrogen or fluorine: $R^4$ is halogen or methyl: $R^5$ is hydrogen, C$_{1-6}$alkyl or C$_{3-10}$alkoxyalkyl: and the salts thereof.

11 Claims, No Drawings

ANTISECRETORY GUANIDINE DERIVATIVES AND PHARMACEUTICAL COMPOSITIONS CONTAINING THEM

This invention relates to guanidine derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, Brit. J. Pharmac., 1966, 27, 427) and the action of histamine at this receptor is blocked (antagonised) by classical "antihistamine" drugs such as mepyramine. The second histamine receptor has been named the H-2 receptor (Black et al., Nature, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In U.K. Pat. Nos. 1,338,169 and 1,397,436 there are described histamine H-2 receptor antagonists which are thiazole derivatives having a side chain in the 4-position, to the end of which is attached, for example, a urea, thiourea, guanidine or N-cyanoguanidine. It has now been discovered that if an optionally-substituted guanidino radical is substituted in the 2-position of such compounds and a benzene ring is inserted in the side chain there are produced compounds which are potent histamine H-2 receptor antagonists.

According to the invention there is provided a guanidine derivative of the formula:

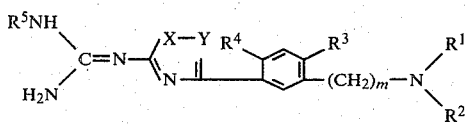

in which X is an oxygen or sulphur atom:

Y is a nitrogen atom or a radical of the formula CH or CCH$_3$:

m is 0 or 1:

R$^1$ is a hydrogen atom and R$^2$ is a cyano, trifluoroacetyl, alkanoyl of 1 to 6 carbon atoms or 4,5-dihydro-4-oxothiazol-2-yl radical or —R$^2$ is a radical of the formula —A—B in which A is a 3,4-dioxocyclobuten-1,2-diyl radical or a radical of the formula C=Z in which Z is an oxygen or sulphur atom or a radical of the formula NCN, NNO$_2$, CHNO$_2$, NCONH$_2$, C(CN)$_2$, NCOR$^6$, NCO$_2$R$^6$, NSO$_2$R$^6$ or NR$^7$ in which R$^6$ is an alkyl radical of 1 to 6 carbon atoms and R$^7$ is a hydrogen atom or an alkyl radical of 1 to 6 carbon atoms and B is an alkyl, alkoxy or alkylthio radical of 1 to 6 carbon atoms or a radical of the formula NR$^8$R$^9$ in which R$^8$ and R$^9$, which may be the same or different, are hydrogen atoms, alkyl radicals of 1 to 10 carbon atoms, alkenyl or alkynyl radicals of 3 to 10 carbon atoms in which the double or triple bond is separated from the nitrogen atom of NR$^8$R$^9$ by at least one carbon atom, (primary hydroxy)alkyl radicals of 2 to 6 carbon atoms, alkoxyalkyl radicals of 3 to 10 carbon atoms in which the oxygen atom is separated from the nitrogen atom of NR$^8$R$^9$ by at least two carbon atoms, or pyridylmethyl radicals, or, when R$^9$ is a hydrogen atom, R$^8$ is a 2-[(5-dimethylaminomethylfuran-2-yl)methylthio]ethylamino radical, or R$^8$ and R$^9$ may be joined together to form a 5- or 6-membered non-aromatic ring which optionally contains an additional nitrogen or oxygen atom; or R$^1$ and R$^2$ are together an imidazolidin-2-ylidene radical:

R$^3$ is a hydrogen or fluorine atom:

R$^4$ is a hydrogen atom or, when R$^3$ is a hydrogen atom, R$^4$ is a halogen atom or a methyl radical:

R$^5$ is a hydrogen atom, an alkyl radical of 1 to 6 carbon atoms or an alkoxyalkyl radical of 3 to 10 carbon atoms in which the oxygen atom is separated from the nitrogen atom of the guanidine residue by at least two carbon atoms:

and the pharmaceutically-acceptable acid-addition salts thereof.

It is to be understood that, in the above formula I and throughout this specification, although the double bonds in both side chains have been inserted in particular positions, various other tautomeric forms are possible, and this invention includes such tautomeric forms within its scope, both in terms of the compound of the invention and in terms of the manufacturing processes.

A particular value for R$^2$ when it is an alkanoyl radical is a formyl or acetyl radical.

A particular value for B when it is an alkyl, alkoxy or alkylthio radical is a methyl, methoxy or methylthio radical and a particular value for B when it is a radical of the formula NR$^8$R$^9$ is an amino, methylamino, dimethylamino, n-propylamino, allylamino, propargylamino, 2-hydroxyethylamino, 2-methoxyethylamino, pyrid-2-ylmethylamino, 2-[(5-dimethylaminomethylfuran-2-yl)methylthio]-ethylamino or morpholino radical.

A particular value for R$^4$ when it is a halogen atom is a bromine atom.

A particular value for R$^5$ when it is an alkyl or alkoxyalkyl radical is a methyl or 2-methoxyethyl radical.

The following are preferred features of the guanidine derivative of the formula I. When any of these features is taken, either singly or in combination with the other general features of the guanidine derivative of the formula I listed above, there are obtained preferred subgroups of compounds within the above definition.

1. X is a sulphur atom and Y is a CH radical.
2. m is O, R$^3$ and R$^4$ are hydrogen atoms and —R$^2$ is a radical of the formula —A—B in which B is an alkyl radical or a radical of the formula NR$^8$R$^9$, or R$^1$ and R$^2$ are together an imidazolidin-2-ylidene radical.
3. A is a radical of the formula C=Z in which Z is an oxygen atom or a radical of the formula NCN, NNO$_2$, CHNO$_2$ or NH and R$^9$ is a hydrogen atom.
4. R$^5$ is a hydrogen atom or a 2-methoxyethyl radical.
5. R$^8$ is a hydrogen atom or a methyl or propargyl radical.

The following compounds are preferred:
2-guanidino-4-(3-guanidinophenyl)thiazole (Example 5);

2-guanidino-4-[3-(N$^2$-cyanoacetamidino)phenyl]-thiazole (Example 15);

2-guanidino-4-[3-(imidazolidin-2-ylideneamino)-phenyl]thiazole (Example 25);

2-[2-(2-methoxyethyl)guanidino]-4-[3-(2-cyano-3-methylguanidino)phenyl]thiazole (Example 24);

2-guanidino-4-[3-(2-cyano-3-propargylguanidino)-phenyl]thiazole (Example 33);

2-guanidino-4-[3-(3-methylureido)phenyl]thiazole (Example 34);

2-guanidino-4-[3-(2-nitroguanidino)phenyl]thiazole (Example 39);

and the pharmaceutically-acceptable acid-addition salts thereof.

The following compounds are particularly preferred:

2-guanidino-4-[3-(2-cyano-3-methylguanidino)-phenyl]-thiazole (Example 2);

1-[3-(2-guanidinothiazol-4-yl)phenylamino]-1-methylamino-2-nitroethylene (Example 18);

and the pharmaceutically-acceptable acid-addition salts thereof.

A particular pharmaceutically-acceptable acid-addition salt of the guanidine derivative of the invention is, for example, a salt formed with hydrochloric, hydrobromic, phosphoric, sulphuric, acetic, citric or maleic acid.

The guanidine derivative of the invention may be manufactured by methods known in themselves for the manufacture of chemically-analogous compounds. The following processes, X,Y,m, $R^1$, $R^2$, $R^3$, $R^4$, $R^5$, $R^6$, $R^7$, $R^8$ and $R^9$ having the meanings stated above unless indicated otherwise, are therefore provided as further features of the invention.

The process of the invention is characterised by:

(a) for a compound in which —$R^2$ is a radical of the formula —A–B in which B is other than an alkyl radical, reaction of a compound of the formula:

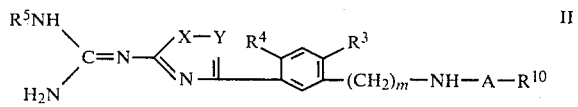

in which $R^{10}$ is a displaceable radical with a compound of the formula $R^{11}$—H in which $R^{11}$ is an alkoxy or alkylthio radical or a radical of the formula $NR^8R^9$;

(b) for a compound in which $R^2$ is a trifluoroacetyl or alkanoyl radical or a radical of the formula A–B, reaction of a compound of the formula:

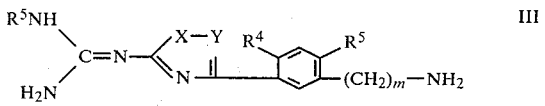

with a compound of the formula $R^{10}$-$R^{12}$ in which $R^{10}$ is a displaceable radical and $R^{12}$ is a trifluoroacetyl or alkanoyl radical of 1 to 6 carbon atoms or a radical of the formula A–B;

(c) for a compound in which —$R^2$ is a radical of the formula —A–B in which A is a radical of the formula C=Z in which Z is an oxygen or sulphur atom and B is a radical of the formula $NR^8R^9$ in which $R^9$ is a hydrogen atom and $R^8$ has the value stated above other than a (primary hydroxy)-alkyl radical, reaction of a compound of the formula III with a compound of the formula $R^{13}$—N=C=D in which D is an oxygen or sulphur atom and $R^{13}$ is a hydrogen atom or an alkyl, alkenyl, alkynyl, alkoxyalkyl, pyridylmethyl or 2-[(5-dimethylaminomethylfuran-2-yl)methylthio]-ethylamino radical;

(d) for a compound in which —$R^2$ is a radical of the formula —A–B in which A is a radical of the formula C=Z in which Z is a radical of the formula NCN and B is a radical of the formula $NR^8R^9$ in which both $R^8$ and $R^9$ are hydrogen atoms, reaction of a compound of the formula III with dicyanimide or a salt thereof;

(e) for a compound in which —$R^2$ is a radical of the formula —A–B in which A is a radical of the formula C=Z in which Z is a sulphur atom or NH radical and B is a radical of the formula $NR^8R^9$ in which $R^8$ and $R^9$ are hydrogen atoms, hydrolysis of the corresponding compound in which the $NH_2$ residue corresponding to $NR^8R^9$ carries an acyl radical;

(f) for a compound in which X is a sulphur atom and Y is a radical of the formula CH or $CCH_3$, reaction of a compound of the formula:

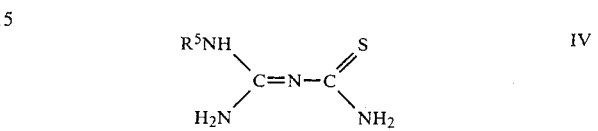

with a compound of the formula:

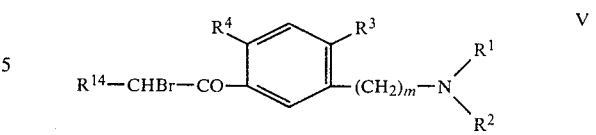

in which $R^{14}$ is a hydrogen atom or a methyl radical;

(g) for a compound in which $R^1$ and $R^2$ are together an imidazolidin-2-ylidene radical, reaction of a compound of the formula I in which —$R^2$ is a radical of the formula —A–B in which A is a radical of the formula C=Z in which Z is a radical of the formula NCN and B is an alkoxy or alkylthio radical with 1,2-diaminoethane;

(h) for a compound in which $R^2$ is a 4,5-dihydro-4-oxothiazol-2-yl radical, reaction of a compound of the formula I in which —$R^2$ is a radical of the formula —A–B in which A is a radical of the formula C=Z in which Z is a sulphur atom and B is a radical of the formula $NR^8R^9$ in which $R^8$ and $R^9$ are both hydrogen atoms with a bromacetic ester;

(i) for a compound in which —$R^2$ is a radical of the formula —A–B in which A is a radical of the formula C=Z in which Z is an oxygen atom and B is a radical of the formula $NR^8R^9$ in which $R^8$ is other than a hydrogen atom, reaction of the corresponding compound in which Z is a sulphur atom with silver nitrate in the presence of water;

(j) for a compound in which $R^2$ is a cyano radical, reaction of the compound of the formula I in which —$R^2$ is a radical of the formula —A–B in which A is a radical of the formula C=Z in which Z is a sulphur atom and B is a radical of the formula $NR^8R^9$ in which $R^8$ and $R^9$ are both hydrogen atoms with silver nitrate:

Whereafter if a salt is required, the compound of the formula I in free base form is reacted with an acid which affords a pharmaceutically acceptable anion.

Process (a) may be carried out using an excess of $R^{11}$—H, that is using an excess of the amine $R^8R^9NH$, optionally in the presence of a diluent or solvent such as water, methanol, ethanol or pyridine, or using an excess of the alcohol $R^{15}$—OH or alkylthio $R^{15}$—SH in which $R^{15}$ is an alkyl radical of 1 to 6 carbon atoms, preferably in the form of a salt such as the sodium salt in the same alcohol or alkylthio as diluent or solvent. $R^{10}$ is preferably an alkoxy or alkylthio radical, for example a methoxy, ethoxy or methylthio radical. Process (b) may be carried out using an excess of the compound of the formula $R^{10}$-$R^{12}$. When $R^{12}$ is a radical of the formula A-B the reaction may be carried out in a diluent or solvent such as methanol, ethanol or dimethylformamide and $R^{10}$ is preferably an alkoxy or alkylthio radical, for example a methoxy or methylthio radical. When $R^{12}$ is a trifluoroacetyl or alkanoyl radical, the reaction may be carried out in a diluent or solvent such as acetic acid or acetonitrile and $R^{10}$ is preferably such a radical that the formula $R^{10}$-$R^{12}$ represents trifluoroacetic anhydride or the alkanoic acid anhydride or the corresponding acid chlorides. Process (c) may be carried out using a molar equivalent of the isocyanate or an excess of the isothiocyanate $R^{13}$-N=C=D. When D is a sulphur atom the reaction is preferably carried out in a diluent or solvent such as methanol, ethanol or dimethylformamide. When D is an oxygen atom a non-alcoholic diluent or solvent must be used.

Process (d) may be carried out using the sodium salt of dicyanimide in a diluent or solvent such as aqueous ethanol.

In process (e) the acyl radical to be hydrolysed is preferably an acetyl or benzoyl radical. The process may be carried out using a dilute base such as sodium hydroxide in a diluent or solvent such as water or aqueous methanol or aqueous ethanol.

Process (f) may be carried out in a diluent or solvent such as ethanol. The starting material of the formula V may be prepared in situ by bromination of the corresponding aceto- or propio-phenone.

Process (g) may be carried out in a diluent or solvent such as methanol.

In process (h), the bromacetic ester used is preferably the ethyl ester. The reaction may be carried out in a diluent or solvent such as methanol and is preferably carried out in the presence of a base such as triethylamine.

Processes (i) and (j) may be carried out in a diluent or solvent such as aqueous dimethylformamide.

Processes (a), (b), (c), (d), (f) and (h) may be accelerated or completed by the application of heat, for example by heating to the boiling point of the diluent or solvent.

The starting material of the formula II for use in process (a) may be prepared by reaction of a compound of the formula III with a compound of the formula $R^{10}$—A–$R^{10}$, for example as set out in Examples 2, 6, 17, 20, 21, 22, 24, 30, 31 or 37.

When Y is a radical of the formula CH or CCH$_3$, the starting material of the formula III for use in process (b), (c) or (d) may be prepared by reaction of a compound of the formula:

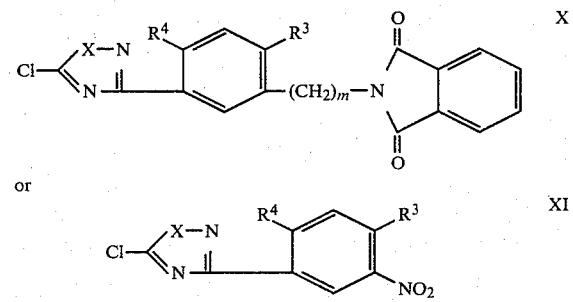

with a compound of the formula:

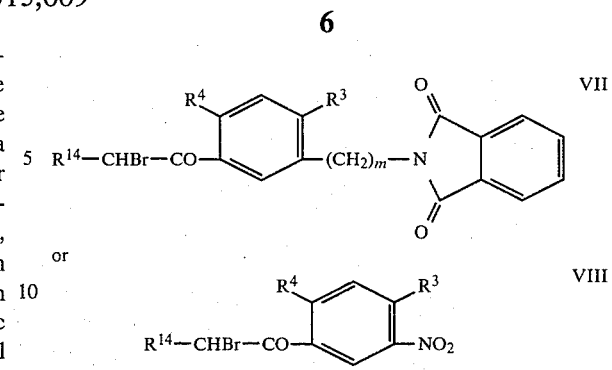

followed by cleavage of the phthalimido residue or reduction of the nitro radical, for example as set out in Examples 1, 6, 19, 20, 24, 30 or 36. When Y is a nitrogen atom, the starting material of the formula III for use in process (b), (c) or (d) may be prepared by reaction of a compound of of the formula:

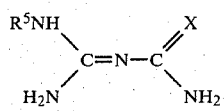

with a compound of the formula:

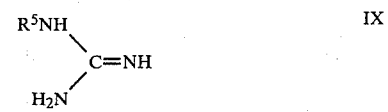

followed by cleavage of the phthalimido residue or reduction of the nitro radical, for example as set out in Example 21.

When Z is an NH radical, the starting material for use in process (e) may be prepared by reaction of an acid-addition salt of the compound of the formula III with an acyl cyanamide, for example as set out in Example 5, or, when Z is a sulphur atom, by reaction of a compound of the formula III with an acyl chloride in the presence of ammonium thiocyanate, for example as set out in Example 16.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastro-intestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced increase in the level of cyclic AMP (in the presence of a phosphodiesterase inhibitor) in a free cell suspension obtained from canine gastric mucosa.

The guinea pig atrium test is carried out as follows:

A guinea pig right atrium is suspended at 1 g. tension (isometric) in a thermostatically-controlled (30° C.) tissue bath (25 ml.) containing oxygenated (95% $O_2$; 5% $CO_2$) Krebs-Hanseleit buffer (pH 7.4). The tissue is allowed to stabilise over 1 hour during which time it is washed 2-4 times. Individual contractions are recorded with a force-displacement transducer through a strain gauge coupler, and instantaneous rates are monitored with a cardiotachometer. A control response to 1 $\mu M$ histamine is obtained after which the tissue is washed 3 times and allowed to re-equilibrate to basal rate. After re-equilibration for 15 minutes, the test compound is added to the desired final concentration. Ten minutes after addition of the compound histamine (1 $\mu M$) is again added and the response to histamine in the presence of antagonist is compared to the histamine control response. The result is expressed as a percentage of the histamine control response. Thereafter the apparent dissociation constant of the H-2 antagonist is determined by standard procedures.

All the compounds exemplified in this specification are active on the guinea pig atrium test at or below a bath concentration of 10 $\mu M$., and the more active compounds show complete inhibition of response at this concentration.

The inhibition of the secretion of gastric acid may be demonstrated in standard tests, for example by the ability of the compound of the formula I, when dosed intragastrically, orally or preferably intravenously, to inhibit the secretion of acidic gastric juice in, for example, rats, cats or dogs provided with gastric fistulae and whose gastric secretion is stimulated by the administration of a secretagogue, for example pentagastrin or histamine.

The test in dogs is carried out as follows:

A female pure bred beagle (9-12 kg.) having a chronic gastric fistula is fasted overnight with water ad lib. During the experiment the dog is light restrained in a standing position. When studying the test compound by the intravenous route, the fistula is opened and, after ascertaining the absence of basal secretion over a period of 30 minutes, a continuous intravenous infusion of secretagogue (0.5 $\mu mole/kg./hour$ of histamine or 2 $\mu g./kg./hour$ pentagastrin) in saline (15 ml./hour) is begun. Gastric acid samples are collected every 15 minutes. The volume of each sample is measured and a 1 ml. aliquot is titrated to neutrality with 0.1 NNaOH to determine acid concentration. When a plateau of secretion is reached, (1-2 hours) the test compound is administered intravenously in saline and gastric acid samples are collected for a further 2-3 hours during which time the infusion of the secretagogue continues uninterrupted.

When studying the test compound by the intragastric route, the absence of basal secretion over a period of 30 minutes is ascertained and the test compound, contained in 25 ml. of 0.5% w/v hydroxypropyl methylcellulose and 0.1% w/v 'Tween' 80 in water ('Tween' is a Trade Mark), is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route, it is administered in a gelatin capsule washed down with 15 ml. of water. One hour later, the fistula is opened and intravenous infusion of the secretagogue is immediately begun. Gastric acid samples are measured as above and the approach of acid secretion to a plateau is compared to that of an undosed control animal.

No overt toxicity or side effects were noted during the dog tests. The compound 2-guanidino-4-[3-(2-cyano-3-methyl-guanidino)phenyl]-thiazole showed no overt toxicity when dosed intraperitoneally to mice at 50 mg./kg.

According to a further feature of the invention there is provided a pharmaceutical composition which comprises a guanidine derivative of the invention in association with a non-toxic pharmaceutically-acceptable diluent or carrier.

The pharmaceutical composition, may, for example, be in the form suitable for oral, rectal, parenteral or topical administration, for which purposes it may be formulated by means known to the art into the form of, for example, tablets, capsules, aqueous or oily solutions or suspensions, emulsions, dispersible powders, suppositories, sterile injectable aqueous or oily solutions or suspension, gels, creams, ointments or lotions.

In addition to the guanidine derivative of the formula I, the pharmaceutical composition of the invention for oral, rectal or parenteral administration may also contain, or be coadministered with, one or more known drugs selected from antacids, for example aluminium hydroxide—magnesium hydroxide mixtures; antipepsin compounds, for example pepstatin; other histamine H-2 antagonists, for example cimetidine; ulcer healing agents, for example dihydrocanadensolide, carbenoxolone or bismuth salts; anti-inflammatory agents, for example ibuprofen, indomethacin, naproxen or aspirin; prostaglandins, for example 16,16-dimethylprostaglandin $E_2$; classical antihistamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical antihistamines (histamine H-1 antagonists), for example mepyramine or diphenhydramine and/or one or more steroidal antiinflammatory agents, for example fluocinolone or triamcinolone.

A topical composition may contain 1-10% w/w of the guanidine derivative of the invention. An oral is, for example, one suitable for oral administration in unit dosage form, for example a tablet or capsule which contains between 100 mg. and 500 mg. of the guanidine derivative of the invention. A preferred pharmaceutical composition of the invention is one suitable for intravenous, subcutaneous or intramuscular injection, for example a sterile injectable containing between 0.1% and 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency of the guanidine derivative of the present invention relative to cimetidine. Thus each patient will receive an oral dose of between 100 mg. and 1500 mg. and preferably between 100 mg. and 300 mg. of guanidine derivative or an intravenous, subcutaneous or intramuscular dose of between 1.5 mg. and 150 mg., and preferably between 5 mg. and 20 mg. of the guanidine derivative, the composition being administered 2 to 4 times per day. The rectal dose will be approximately the same as the oral dose.

The invention is illustrated, but not limited, by the following Examples in which Example 1 describes the preparation of starting material:

EXAMPLE 1

A mixture of 2-guanidino-4-(3-phthalimidophenyl)-thiazole hydrobromide (10 g.), concentrated hydrochloric acid (150 ml.) and glacial acetic acid (150 ml.) was heated for 18 hours on a steam bath. The mixture was evaporated to dryness, and the residual solid suspended in ethanol and filtered. The resulting solid, the hydrochloride hydrobromide salt of the product, was dissolved in water (150 ml.) and excess sodium hydroxide solution added. The white precipitate that formed was filtered, washed with water and recrystallised from acetonitrile to give 2.9 g. of 2-guanidino-4-(3-aminophenyl)thiazole, m.p. 223°–224° C.

The 2-guanidino-4-(3-phthalimidophenyl)-thiazole hydrobromide used as starting material may be prepared as follows:

A solution of 3-phthalimidoacetophenone (26.5 g.) in chloroform (250 ml.) was stirred and a solution of hydrobromic acid in acetic acid (45% w/v, 0.5 ml.) added. Bromine (16.0 g.) was then added slowly over approximately 15 minutes. The solution was then evaporated to dryness, the residual solid dissolved in refluxing acetonitrile, and the hot solution added cautiously to a stirred solution of amidinothiourea (11.8 g.) in hot ethanol (400 ml.). After the addition, the mixture was stirred and heated under reflux for 1 hour and cooled to room temperature. The white precipitate of 2-guanidino-4-(3-phthalimidophenyl)thiazole hydrobromide was filtered off and washed with ethanol, m.p. >300° C.

EXAMPLE 2

A mixture of 2-guanidino-4-[3-(3-cyano-2-methylisothioureido)phenyl]thiazole (5 g.) and 33% w/v ethanolic methylamine (100 ml.) was stirred overnight. The resulting solution was then treated with charcoal, stirred for 2 minutes, filtered and the filtrate evaporated to dryness. The residual gum was dissolved in acetone (70 ml.) and the solution stirred for 1 hour. The crystalline product was filtered off and recrystallised from dimethylformamide/water to give 3 g. of 2-guanidino-4-[3-(2-cyano-3-methylguanidino)phenyl]thiazole, m.p. 260°–263° C.

The 2-guanidino-4-[3-(3-cyano-2-methylisothioureido)phenyl]thiazole used as starting material may be prepared as follows:

A mixture of 2-guanidino-4-(3-aminophenyl) thiazole (8.7 g.) and dimethyl (cyanoimido)dithiocarbonate (5.4 g.) in methanol (70 ml.) was heated under reflux. After 2 hours boiling the white precipitate was filtered from the hot suspension, washed with methanol, suspended in hot acetone and filtered. The resulting solid (5.5 g.) was recrystallised by adding acetone to a solution in dimethylformamide. The product had m.p. >300° C.

EXAMPLE 3

A mixture of 4-(3-aminophenyl)-2-guanidinothiazole (1.3 g.) and methylisothiocyanate (0.7 g.) in dimethylformamide (10 ml.) was heated at 90° C. for 1 hour. The dimethylformamide was then removed by evaporation, and the residual gum dissolved in ethanol. Sufficient saturated ethanolic oxalic acid was added to precipitate a white solid. This was filtered off and washed with ethanol to give 0.2 g. of 2-guanidino-4-[3-(3-methylthioureido)phenyl]thiazole oxalate, m.p. 219°–222° C. (decomp.).

EXAMPLE 4

A mixture of 4-(3-aminophenyl)-2-guanidinothiazole dihydrochloride (2.4 g.) (prepared from the free base by dissolving it in concentrated HCl and evaporating to dryness) and sodium dicyanimide (1.0 g.) in water (20 ml.) was heated at 90° C. After 15 minutes sufficient ethanol was added to achieve a single phase. After heating for a further 2 hours, the mixture was cooled, and the pH adjusted to 11 with dilute sodium hydroxide solution. The precipitate that formed was filtered and washed with methanol. The filtrate was evaporated to half volume, and extracted with ethyl acetate (2×20 ml.). The ethyl acetate was evaporated to dryness to give a white foam. This on triturating with hot ethanol gave 0.9 g. of 2-guanidino-4-[3-(2-cyanoguanidino)-phenyl]thiazole which had m.p. 247°–251° C. on recrystallisation from dimethylformamide/water.

EXAMPLE 5

A solution of 2-guanidino-4-[3-(2-benzoylguanidino)-phenyl]thiazole (0.9 g.) in dilute sodium hydroxide (20 ml.) was allowed to stand at room temperature for 4 days. The precipitated white solid was filtered off, washed with water and dried to give 0.3 g. 2-guanidino-4-(3-guanidinophenyl)thiazole, m.p. 255°–260° C. (decomp.).

The 2-guanidino-4-[3-(2-benzoylguanidino)phenyl]-thiazole used as starting material may be obtained as follows:

A mixture of 2-guanidino-4-(3-aminophenyl)-thiazole hydrochloride hydrobromide (1.2 g.) and benzoylcyanamide (0.7 g.) in dimethylformamide (15 ml.) and water (10 ml.) was heated at 90° C. for 2 hours. The mixture was diluted with water (30 ml.) and made strongly basic with dilute sodium hydroxide solution. The mixture was extracted with ethyl acetate (2×50 ml.) and the extract evaporated to dryness to give 2-guanidino-4-[3-(2-benzoylguanidino)phenyl]-thiazole as a dark gum (0.9 g.)

EXAMPLE 6

A suspension of 2-guanidino-4-[3-(3-cyano-2-methylisothioureidomethyl)phenyl]thiazole in ethanol was mixed with 33% w/v ethanolic methylamine (20 ml.). After 3 hours the resulting solution was evaporated to dryness and the residual gum was recrystallised from acetonitrile to give 0.35 g. of 2-guanidino-4-[3-(2-cyano-3-methylguanidinomethyl)phenyl]thiazole, m.p. 208°–211° C.

The 2-guanidino-4-[3-(3-cyano-2-methylisothioureidomethyl)phenyl]thiazole used as starting material may be prepared as follows:

A mixture of 3-phthalimidomethylphenacyl chloride (3.2 g.) and amidinothiourea (1.2 g.) in ethanol (60 ml.) was heated under reflux for 1 hour. The mixture was cooled and the white crystalline 2-guanidino-4-(3-phthalimidomethylphenyl)thiazole hydrochloride, (3 g.), m.p. 248°–252° C., filtered off.

A mixture of 2-guanidino-4-(3-phthalimidomethyl-phenyl)thiazole hydrochloride (0.7 g.) in water (30 ml.) and ethanol (30 ml.) and sufficient aqueous sodium hydroxide to give pH 12 was heated under reflux for 30 minutes. The pH was adjusted to approximately 3 with concentrated hydrochloric acid and the mixture heated under reflux for a further 30 minutes. The pH was then adjusted to 12 with dilute sodium hydroxide solution and the mixture extracted with ethyl acetate (50 ml.). This extract was evaporated to dryness to give 2-guanidino-4-(3-aminomethylphenyl)thiazole (0.15 g.), m.p. 155°–160° C. (decomp.).

To a solution of 2-guanidino-4-(3-aminomethyl-phenyl)thiazole (0.5 g.) in warm ethanol (10 ml.) was added dimethyl (cyanoimido)dithiocarbonate (0.3 g.). The mixture was stirred for 1 hour during which time a precipitate gradually formed. This precipitate was filtered off to give 2-guanidino-4-[3-(3-cyano-2-methyliso-thioureidomethyl)phenyl]thiazole.

EXAMPLE 7

To a solution of 2-guanidino-4-(3-aminophenyl)-thiazole (0.24 g.) in acetic acid (5 ml.) was added acetic anhydride (0.25 g.). The mixture was allowed to stand for 18 hours and the white solid precipitate (0.25 g.) was filtered off to give 2-guanidino-4-(3-acetylamino-phenyl)thiazole diacetate, m.p. 171°–173° C., solidifies and remelts at 258°–261° C.

EXAMPLE 8

A mixture of 2-guanidino-4-(3-aminophenyl)-thiazole (1.2 g.) and trifluoroacetic anhydride (1.05 g.) was heated under reflux in acetonitrile for 3 hours. The mixture was cooled and the product (0.76 g.) filtered off to give 2-guanidino-4-(3-trifluoroacetylaminophenyl)-thiazole trifluoroacetate, m.p. 152°–153° C.

EXAMPLE 9

To a solution of 3-formylaminoacetophenone (1.2 g.) in dichloromethane (10 ml.) was added bromine (1.2 g.). After stirring and heating under reflux for 30 minutes the mixture was evaporated to dryness and the residue of 3-formylaminophenacyl bromide was added to amidinothiourea (0.91 g.) in ethanol (20 ml.). The mixture was heated under reflux for 1 hour cooled and the product filtered off to give 0.47 g. of 2-guanidino-4-(3-formylaminophenyl)-thiazole hydrobromide, m.p. 244°–245° C.

EXAMPLE 10

A mixture of 2-guanidino-4-[3-(3-cyano-2-methyliso-thioureido)phenyl]thiazole (0.29 g.) and 30% w/v ethanolic dimethylamine (30 ml.) was allowed to stand overnight. The solution was evaporated to dryness and the residue dissolved in ethanol (20 ml.) at reflux. The solution deposited crystals on standing overnight at room temperature and the solid was filtered off, washed with ethanol and air-dried to give 0.25 g. of 2-guanidino-4-[3-(2-cyano-3,3-dimethylguanidino)-phenyl]thiazole, m.p. 241°–243° C. (decomp.).

EXAMPLE 11

A mixture of 2-guanidino-4-[3-(3-cyano-2-methyliso-thioureido)phenyl]thiazole (0.67 g.) and n-propylamine (10 ml.) was stirred for 24 hours. The clear solution was evaporated and the residual gum dissolved in ethanol (20 ml.). After stirring briefly a crystalline product formed. This was filtered off, washed with ethanol and air-dried to give 0.55 g. of 2-guanidino-4-[3-(2-cyano-3-propylguanidino)phenyl]thiazole, m.p. 232°–234° C.

EXAMPLE 12

A mixture of 2-guanidino-4-[3-(3-cyano-2-methyliso-thioureido)phenyl]thiazole (0.67 g.) ethanol (5 ml.) and ethanolamine (5 ml.) was stirred at room temperature for 3 days. The resulting solution was evaporated to dryness and the residual gum triturated with water. The water was discarded and the residual gum dissolved in ethanol (10 ml.) The solution deposited crystals on standing briefly. The product was filtered off, washed with ethanol and air-dried to give 0.25 g. of 2-guanidino-4-[3-(2-cyano-3-(2-hydroxyethyl)guanidino)-phenyl]thiazole, m.p. 209°–211° C.

EXAMPLE 13

A mixture of 2-guanidino-4-[3-(3-cyano-2-methyliso-thioureido)phenyl]thiazole (0.67 g.) ethanol (5 ml.) and 2-methoxyethylamine (5 ml.) was stirred for 24 hours. The solution was then evaporated and the residual gum dissolved in acetone (20 ml.). The solution deposited crystals on stirring and the solid was filtered off, washed with ethanol and air-dried to give 0.4 g. of 2-guanidino-4-[3-(2-cyano-3-(2-methoxyethyl)-guanidino)phenyl]thiazole, m.p. 255°–256° C.

EXAMPLE 14

A mixture of 2-guanidino-4-[3-(3-cyano-2-methyliso-thioureido)phenyl]thiazole (0.6 g.), methanol (10 ml.) and allylamine (10 ml.) was stirred for 3 days. The resulting solution was evaporated to dryness and the residual gum dissolved in ethanol (10 ml.). The solution deposited crystals on standing overnight and the product was filtered off, washed with ethanol and air-dried to give 0.25 g. of 2-guanidino-4-[3-(2-cyano-3-allyl-guanidino)phenyl]thiazole, m.p. 224°–226° C.

EXAMPLE 15

A mixture of 2-guanidino-4-(3-aminophenyl)-thiazole (0.47 g.), dimethylformamide (2 ml.) and ethyl N-cyanoacetimidate (0.26 g.) was allowed to stand at room temperature for 4 days. The crystalline product was filtered off, washed with methanol and air-dried to give 0.2 g. of 2-guanidino-4-[3-($N^2$-cyanoacetamidino)-phenyl]thiazole containing one molecule of dimethylformamide of crystallisation, m.p. 265°–270° C.

EXAMPLE 16

A mixture of 2-guanidino-4-[3-(3-benzoylthioureido)-phenyl]thiazole (1.5 g.), methanol (5 ml.) and aqueous 2 N sodium hydroxide (5 ml.) was stirred for 30 minutes. The precipitated solid was filtered off, washed with aqueous methanol and air dried to give 0.62 g. of 2-guanidino-4-(3-thioureidophenyl)-thiazole, m.p. 198°–200° C. (decomp.).

The 2-guanidino-4-[3-(3-benzoylthioureido)-phenyl]-thiazole used as starting material may be prepared as follows:

Benzoyl chloride (0.7 g.) was added dropwise to a stirred mixture of ammonium thiocyanate (0.38 g.) in acetone (25 ml.). After addition the mixture was stirred for 15 minutes, and then 2-guanidino-4-(3-aminophenyl)thiazole (1.12 g.) was added and the mixture heated under reflux for 30 minutes. The mixture was then cooled and the precipitated solid filtered off, washed with water and air-dried to give 1.59 g. of 2-guanidino-4-[3-(3-benzoylthioureido)phenyl]-thiazole.

EXAMPLE 17

A mixture of 2-guanidino-4-(3-amino-phenyl)thiazole (1.17 g.) and 1,1-di(methylthio)-2-nitroethylene (0.9 g.) was heated under reflux in methanol (25 ml.) overnight. The resulting yellow precipitate was filtered off, washed with methanol and air-dried to give 1.25 g. of 1-[3-(2-guanidinothiazol-4-yl)phenylamino]-1-methylthio-2-nitroethylene, m.p. 215° C. (decomp).

EXAMPLE 18

A mixture of 1-[3-(2-guanidinothiazol-4-yl)phenylamino]-1-methylthio-2-nitroethylene (0.9 g.) and 33% w/v ethanolic methylamine (30 ml.) was allowed to stand at room temperature for 3 days. The mixture was then evaporated to dryness, the residue dissolved in refluxing methanol (10 ml.) and the solution cooled. The resulting precipitate was filtered off, washed with ethanol and air-dried to give 0.45 g. of 1-[3-(2-guanidinothiazol-4-yl)phenylamino]-1-methylamino-2-nitroethylene, m.p. 250° C. (decomp.).

EXAMPLE 19

A mixture of 2-guanidino-4-(3-aminophenyl-5-methylthiazole dihydrochloride (0.67 g.), triethylamine (1 ml.) and methylisothiocyanate (0.15 g.) was heated in dimethylformamide (5 ml.) at 90° C. for 30 minutes. The clear solution was then poured into water (20 ml.) and the mixture extracted with chloroform (2×30 ml). The organic layers were combined and evaporated. The residual gum was dissolved in ethanol (10 ml.) and just sufficient ethanolic oxalic acid solution added to precipitate the product. This was filtered off, washed with ethanol and air-dried to give 0.24 g. of 2-guanidino-4-[3-(3-methylthioureido)phenyl]-5-methylthiazole oxalate, m.p. 191°–195° C. (decomp).

The 2-guanidino-4-(3-aminophenyl)-5-methylthiazole dihydrochloride used as starting material may be prepared as follows:

To a stirred mixture of m-nitropropiophenone (3.6 g.) in chloroform (50 ml.) was added 3 drops of a solution of hydrogen bromide in acetic acid (45% w/v). Bromine (3.2 g.) in chloroform (10 ml.) was then added dropwise. After addition the mixture was stirred until colourless, evaporated to dryness, the residue dissolved in ethanol (50 ml.) and this solution added to amidinothiourea (2.4 g.) in ethanol (150 ml.) at reflux. The mixture was heated under reflux for 30 minutes and then evaporated to approximately 50 ml. On standing overnight at room temperature a crystalline solid was produced. This was filtered off, washed with ethanol and air-dried to give 6.05 g. of 2-guanidino-4-(3-nitrophenyl)-5-methylthiazole hydrobromide, m.p. 217°–222° C.

A mixture of 2-guanidino-4-(3-nitrophenyl)-5-methylthiazole (2.0 g.) acetic acid (40 ml.) and water (10 ml.) was stirred and heated under reflux. Iron powder (3.0 g.) was added and heating continued for 1 hour. The mixture was then evaporated. The residue was suspended in water (100 ml.) and basified with dilute aqueous sodium hydroxide to a pH of approximately 12. The mixture was extracted with ethyl acetate (2×200 ml.). The organic layers were separated, filtered and evaporated to give a yellow foam. This was heated in a mixture of concentrated hydrochloric acid (50 ml.) and acetic acid (50 ml.) for 2 hours at 90° C. and then evaporated to give 1.7 g. of 2-guanidino-4-(3-aminophenyl)-5-methylthiazole dihydrochloride. A sample converted to free base by addition to aqueous sodium hydroxide and recrystallised from acetonitrile had m.p. 223°–225° C.

EXAMPLE 20

A mixture of 2-(2-methylguanidino)-4-(3-aminophenyl)thiazole (1.1 g.) and dimethyl(cyanoimido)dithiocarbonate (0.7 g.) was heated under reflux in methanol (10 ml.) for 5 hours. The mixture was cooled and the white precipitate of 2-(2-methylguanidino)-4-[3-(3-cyano-2-methylisothioureido)phenyl]thiazole was filtered off and dissolved in 33% w/v ethanolic methylamine (20 ml.). After 4 hours the precipitated solid was filtered off, washed with ethanol and air-dried to give 0.8 g. of 2-(2-methylguanidino)-4-[3-(2-cyano-3-methylguanidino)phenyl]thiazole, m.p. 170°–173° C.

The 2-(2-methylguanidino)-4-(3-aminophenyl)-thiazole used as starting material may be prepared as follows:

A solution of 3-phthalimidophenacylbromide (10.4 g.) in hot acetonitrile (70 ml.) was added to (N-methylamidino)thiourea (4.4 g.) in ethanol (100 ml.) heated under reflux and the mixture was heated under reflux for 30 minutes and then cooled. The crystalline product was filtered off, washed with ethanol and air-dried to give 11.6 g. of 2-(2-methylguanidino)-4-(3-phthalimidophenyl)thiazole hydrobromide, m.p. 300° C.

A mixture of 2-(2-methylguanidino)-4-(3-phthalimidophenyl)thiazole hydrobromide (11.0 g.), acetic acid (100 ml.) and concentrated hydrochloric acid (100 ml.) was heated overnight at 90° C. The clear solution was evaporated to dryness and the residue triturated with ethanol. The solid product was filtered off, dissolved in water (100 ml.) and dilute aqueous sodium hydroxide was added to precipitate a white solid. This was filtered off, dissolved in methanol (30 ml.) under reflux and cooled. The product was filtered off and air-dried to give 1.8 g. of 2-(2-methylguanidino)-4-(3-aminophenyl)thiazole, m.p. 182°–182° C.

EXAMPLE 21

A mixture of 3-(3-aminophenyl)-5-guanidino-1,2,4-thiadiazole (1 g.) and 1,1-di(methylthio)-2-nitroethylene (0.9 g.) was heated under reflux in methanol (20 ml.) for 5 hours. The resulting yellow precipitate of 1-[3-(5-guanidino-1,2,4-thiadiazol-4-yl)phenylamino]-1-methylthio-2-nitroethylene was filtered off, washed with methanol and stirred overnight in 33% w/v ethanolic methylamine (40 ml.). The clear solution was then evaporated and the residue triturated with ethanol. The resulting yellow solid was filtered off, washed with ethanol and air-dried to give 0.5 g. of 1-[3-(5-guanidino-1,2,4-thiadiazol-3-yl)phenylamino]-1-methylamino-2-nitroethylene, m.p. 255° C. (decomp.).

The 3-(3-aminophenyl)-5-guanidino-1,2,4-thiadiazole used as starting material may be prepared as follows:

To sodium hydride (50% w/w dispersion in oil, 3.8 g.) in dimethylformamide (125 ml.) was added guanidine nitrate (14.7 g.) in small portions. After evolution of hydrogen had ceased, a solution of 3-(3-nitrophenyl)-5-chloro-1,2,4-thiadiazole (9.6 g.) in dimethylformamide (100 ml) was added dropwise over 30 minutes. This mixture was stirred at room temperature for 2 hours, then heated to 90° C. and sufficient water added to produce a slight precipitate, and the mixture was then cooled. The yellow precipitate was filtered off, washed with water and ethanol and air-dried to give 7.5 g. of 3-(3-nitrophenyl)-5-guanidino-1,2,4-thiadiazole. A sample recrystallised from dimethylformamide/water had m.p. >300° C.

To a mixture of 3-(3-nitrophenyl)-5-guanidino-1,2,4-thiadiazole (1 g.), acetic acid (15 ml.) and water (2 ml.) was added iron powder (1.5 g.). The mixture was heated briefly to 90° C. and then allowed to cool to room temperature over 3 hours. The mixture was then evaporated to dryness, the residue triturated with water (20 ml.) and the pH of the mixture adjusted to 11 with dilute aqueous sodium hydroxide. The mixture was then extracted with ethyl acetate (2×50 ml.) and the combined ethyl acetate extracts were filtered and evaporated to dryness to give 0.5 g. of 3-(3-aminophenyl)-5-guanidino-1,2,4-thiadiazole. A sample of di(hydrogen maleate) salt had m.p. 185° C. (decomp.).

EXAMPLE 22

A mixture of 3-(3-aminophenyl)-5-guanidino-1,2,4-thiadiazole (1.0 g.) and dimethyl(cyanoimido)dithiocarbonate (0.75 g.) was heated under reflux in methanol (15 ml.) for 6 hours. The mixture was cooled and ethyl acetate (30 ml.) added. The precipitated solid was filtered off and air-dried to give 1.0 g. of 3-[3-(3-cyano-2-methylisothioureido)phenyl]-5-guanidino-1,2,4-thiadiazole, m.p. 125° C. (decomp.).

EXAMPLE 23

A mixture of 3-[3-(3-cyano-2-methylisothioureido)phenyl]-5-guanidino-1,2,4-thiadiazole (0.8 g.) and 33% w/v ethanolic methylamine (15 ml.) was allowed to stand overnight. The solution was then filtered and evaporated to dryness. The residue was triturated with a small volume of ethanol and the solid product filtered and air-dried to give 0.45 g. of 3-[3-(2-cyano-3-methylguanidino)phenyl]-5-guanidino-1,2,4-thiadiazole, m.p. 264°-266° C.

EXAMPLE 24

A mixture of 2-[2-(2-methoxyethyl)guanidino]-4-(3-aminophenyl)thiazole (0.63 g.) and dimethyl(cyanoimido)dithiocarbonate (0.3 g.) was heated under reflux in methanol for 6 hours. The mixture was then cooled and the white precipitate of 2-[2-(2-methoxyethyl)guanidino]-4-[3-(3-cyano-2-methylisothioureido)phenyl]thiazole filtered off and stirred in 33% w/v ethanolic methylamine (10 ml.) overnight. The solution was then evaporated and the residue dissolved in ethanol (10 ml.) and on standing this solution deposited a white solid. This was filtered off and air-dried to give 0.25 g. of 2-[2-(2-methoxyethyl)guanidino]-4-[3-(2-cyano-3-methylguanidino)phenyl]-thiazole, m.p. 182°-184° C.

The 2-[2-(2-methoxyethyl)guanidino]-4-(3-aminophenyl)thiazole used as starting material may be prepared as follows:

A mixture of 2-methoxyethylamine (25.3 g.) and concentrated hydrochloric acid (35 ml.) was evaporated to dryness. The residue was heated under reflux overnight in ethanol (100 ml.) with sodium dicyanimide (30 g.). The white precipitate was filtered and washed with ethanol. The combined filtrates were then evaporated to yield 1-(2-methoxyethyl)-2-cyanoguanidine as a crude oil. A mixture of (2-methoxyethyl)cyanoguanidine (19.4 g), water (30 ml.) and concentrated hydrochloric acid (15 ml.) was stirred until a clear solution resulted. Thioacetamide (10.4 g.) was added in small portions. After addition the mixture was stirred for 3 hours and concentrated hydrochloric acid (3 ml.) then added. The solution was heated to 90° C. and filtered and the filtrate basified with concentrated aqueous ammonia to pH 11. The mixture was evaporated to dryness and the residue was triturated with ethanol and filtered. The filtrate was dried over magnesium sulphate, refiltered and evaporated to dryness to give 22.8 g. of crude oil. This was purified by conversion to the oxalate salt in acetone and then reconversion of the isolated salt to free base. This process yielded a N-(2-methoxyethyl)amidimothiourea as an oil.

A solution of 3-phthalimidophenacyl bromide (4.9 g.) in hot acetonitrile (50 ml.) was added to a solution of N-(2-methoxyethyl)amidinothiourea. The resulting solution was heated under reflux for 30 minutes and then evaporated to dryness. The residue was triturated with ethyl acetate to give on filtration 5.7 g. of 2-[2-(2-methoxyethyl)guanidino]-4-(3-phthalimidophenyl)-thiazole hydrobromide, m.p. 245°-248° C. (decomp.).

To a suspension of 2-[2-(2-methoxyethyl)-guanidino]-4-(3-phthalimidophenyl)thiazole hydrobromide (5.5 g.) in a mixture of ethanol (25 ml.) and water (25 ml.) was added sufficient dilute aqueous sodium hydroxide to obtain a pH of 11. The mixture was heated under reflux for 30 minutes, the pH adjusted to 3 with concentrated hydrochloric acid and the mixture heated under reflux for a further 30 minutes. The solution was then evaporated to dryness. The residue was stirred in a small volume of water and sufficient dilute aqueous sodium hydroxide added to produce a pH of 11. The aqueous solution was then extracted with ethyl acetate (3×50 ml.) and the organic extracts were combined and evaporated to give 2.0 g. of 2-[2-(2-methoxyethyl)guanidino]-4-(3-aminophenyl)-thiazole as a yellow foam.

EXAMPLE 25

A solution of 2-guanidino-4-[3-(3-cyano-2-methylisothioureido)phenyl]thiazole (0.6 g.) in a mixture of 1,2-diaminoethane (10 ml.) and methanol (10 ml.) was allowed to stand at room temperature for 5 days. The mixture was then evaporated to dryness on a boiling water bath under reduced pressure. The residual gum was triturated with water, the water was discarded and the residual gum then triturated with acetonitrile. The solid product was filtered and recrystallised from acetonitrile/ethanol to give 0.2 g. of 2-guanidino-4-[3-(imidazolidin-2-ylideneamino)phenyl]thiazole, m.p. 157°-159° C.

EXAMPLE 26

A mixture of 2-guanidino-4-[3-(3-cyano-2-methylisothioureido)phenyl]thiazole (0.66 g.) and 2-aminomethylpyridine (5 ml.) was allowed to stand at room temperature overnight. The solution was then evaporated to dryness and the residue stirred in water (20 ml.). The precipitated solid was filtered off and heated under reflux in methanol. This produced a crystalline solid which was filtered off to give 0.55 g. of 2-guanidino-4-[3-(2-cyano-3-(2-pyridylmethyl)guanidino)phenyl]-thiazole, m.p. 253° C. (decomp.).

EXAMPLE 27

A mixture of 2-guanidino-4-[3-(3-cyano-2-methylisothioureido)phenyl]thiazole, morpholine (10 ml.) and ethanol (10 ml.) was stirred at room temperature for 7 days. The mixture was then evaporated to dryness, the residual gum dissolved in ethanol (15 ml.) and the solution stirred briefly. The precipitate which formed was filtered and air-dried to give 0.35 g. of 2-guanidino-4-[3-

($N^2$-cyanomorpholinoamidino)phenyl]thiazole, m.p. 205°–210° C. (decomp).

EXAMPLE 28

To a solution of 2-guanidino-4-(3-aminomethylphenyl)thiazole (0.5 g.) in ethanol (15 ml.) was added methylisothiocyanate (0.2 g.). The resulting solution was heated under reflux overnight and then evaporated to dryness. The residue was purified by chromatography on silica gel using chloroform/methanol/concentrated aqueous ammonia 800/200/5 v/v/v as eluting solvent. The appropriate fractions were evaporated to dryness. The residual foam was dissolved in ethanol (20 ml.) and a solution of oxalic acid in ethanol was added to precipitate a white solid. This was filtered off and washed with ethanol to give 0.22 g. of 2-guanidino-4-[3-(3-methylisothioureidomethyl)phenyl]thiazole oxalate, m.p. 233°–236° C. (decomp.).

EXAMPLE 29

A mixture of 2-guanidino-4-(3-thioureidophenyl)thiazole (0.9 g.), ethyl bromoacetate (0.34 ml.) and triethylamine (2 ml.) was heated under reflux in methanol (25 ml.) for 30 minutes. The resulting clear solution was evaporated to a low volume and the precipitated white solid was filtered off. The solid was washed with water, dried and dissolved in the minimum quantity of cold dimethylformamide. To this solution was added approximately four times the quantity of ethanol which precipitated a white solid. This was filtered off to give 0.4 g. of 2-guanidino-4-[3-[(4,5-dihydro-4-oxothiazol-2-yl)amino]phenyl]thiazole, m.p. 256° C.

EXAMPLE 30

A mixture of 2-guanidino-4-(2-amino-5-methylphenyl)thiazole (0.8 g.) and dimethyl(cyanoimido)dithiocarbonate (0.55 g.) was heated under reflux overnight in methanol (10 ml.). The mixture was then evaporated to dryness and the residue of 2-guanidino-4-[2-(3-cyano-2-methylisothioureido)-5-methylphenyl]thiazole was allowed to stand for 3 days in 33% w/v ethanolic methylamine (20 ml.). The clear solution was then evaporated to dryness and the residue purified by chromatography on silica using chloroform/methanol/concentrated aqueous ammonia 425:75:3 v/v/v as eluant to give 0.5 g. of a gum. This was dissolved in acetone and an excess of maleic acid in acetone was added. The precipitated solid was filtered off to give 0.29 g. of 2-guanidino-4-[2-(2-cyano-3-methylguanidino-5-methylphenyl]thiazole hydrogen maleate, m.p. 182°–185° C. (decomp.).

The 2-guanidino-4-(2-amino-5-methylphenyl)thiazole used as starting material may be prepared as follows:

To a solution of 2-methyl-5-nitroacetophenone (2.5 g.) in chloroform (50 ml.) was added 2 drops of 45% w/v hydrogen bromide in acetic acid. Bromine (0.75 ml.) was then added dropwise. After the addition the mixture was stirred until the colour of bromine disappeared. The clear solution was then evaporated and the residue dissolved in acetonitrile (25 ml.) and added to a solution of amidinothiourea (1.7 g.) in hot ethanol (50 ml.). The mixture was then heated under reflux for 15 minutes, cooled and the precipitate was filtered off and air-dried to give 3.25 g. of 2-guanidino-4-(2-methyl-5-nitrophenyl)thiazole hydrobromide.

A mixture of 2-guanidino-4-(2-methyl5-nitrophenyl)thiazole hydrobromide (3.1 g.), acetic acid (50 ml.) and water (5 ml.) was stirred at 90° C. Iron powder (3 g.) was added. The mixture was stirred for 15 minutes without further heating. The solution was then evaporated and the residue was triturated with water (30 ml.). The mixture was adjusted to pH 11 with dilute aqueous sodium hydroxide and methanol (100 ml.) then added. The thick suspension was filtered and the filtrate evaporated to a low volume. The resulting white precipitate was filtered off, washed with water and air-dried to give 1.6 g. of 2-guanidino-4-(2-amino-5-methylphenyl)thiazole, m.p. 190° C. (decomp.).

EXAMPLE 31

A mixture of 2-guanidino-4-(3-aminophenyl)thiazole (1.17 g.) and 1,2-dimethoxycyclobutene-3,4-dione (0.7 g.) was heated under reflux in methanol (25 ml.) for 2 hours. The white precipitate of 1-[3-(2-guanidinothiazol4-yl)phenylamino]-2-methoxycyclobutene-3,4-dione was filtered off and stirred in 33% w/v ethanolic methylamine (25 ml) overnight. The precipitated solid was filtered off, washed with methanol and air-dried to give 1.35 g. of 1-[3-(2-guanidinothiazol-4-yl)phenylamino]-2-methylaminocyclobutene3,4-dione, m.p.>300° C.

EXAMPLE 32

A mixture of 2-guanidino-4-(3-amino4-fluorophenyl)thiazole (0.5 g.) and methylisothiocyanate (0.2 g.) was heated at 90° C. in dimethylformamide (5 ml.) for 3 hours. The mixture was then evaporated to dryness and the residue triturated with water to give a white solid. This was purified by preparative thin layer chromatography on silica plates using chloroform/methanol/concentrated aqueous ammonia 800:200:5 v/v/v as developing solvent. This produced a gum which crystallised on trituration with water. The solid was filtered off and air-dried to give 0.095 g. of 2-guanidino-4-[3-(2-methylthioureido)-4-fluorophenyl]thiazole, m.p. 194° C. (decomp.).

The 2-guanidino-4-(3-amino-4-fluorophenyl)thiazole used as starting material may be prepared as follows:

To a solution of 3-fluoro-4-nitroacetophenone (6 g.) in chloroform (40 ml.) was added 2 drops of hydrogen bromide in acetic acid (45% w/v) followed by bromine (1.75 ml.) added dropwise. After the bromine colour had disappeared the clear yellow solution was evaporated to dryness and the residue, dissolved in hot ethanol (40 ml.), was added to amidinothiourea (4.0 g.) in ethanol (100 ml.) under reflux. The mixture was heated under reflux for 15 minutes and then cooled to room temperature. The crystalline solid was filtered off to give 8.8 g. of 2-guanidino4-(3-fluoro-4-nitrophenyl)thiazole hydrobromide, m.p. 248°–252° C.

A mixture of 2-guanidino-4-(3-fluoro-4-nitrophenylthiazole hydrobromide (8 g.) hot acetic acid (100 ml.) and iron dust (12 g.) was stirred for 1 hour. The mixture was then evaporated to dryness, the residue triturated with water (20 ml.) and the pH adjusted to 11 with dilute aqueous sodium hydroxide. The resulting suspension was extracted with ethyl acetate (2×100 ml.) and the combined organic layers were filtered and evaporated to dryness to give 1.5 g. of 2-guanidino4-(3-amino-4-fluorophenyl)thiazole, m.p. 238° C. (decomp.).

EXAMPLE 33

A mixture of 2-guanidino-4-[3-(3-cyano2-methylisothioureido)phenyl]thiazole (0.5 g.), propargylamine hydrochloride (1.45 g.) and triethylamine (3 ml.) was stirred overnight in methanol (5 ml.). The mixture was then evaporated to dryness and the residue triturated successively with water, ethyl acetate and acetonitrile to give a solid. This was filtered off and air-dried to give 0.075 g. of 2-guanidino-4-[3-(2-cyano3-propargyl-guanidino)phenyl]thiazole, m.p. >300° C.

EXAMPLE 34

To a solution of 2-guanidino-4-[3-(3-methylthioureido)phenyl]thiazole (0.6 g.) in dimethylformamide (20 ml.) and water (10 ml.) was added a solution of silver nitrate (0.68 g.) in water (2 ml.). The mixture was allowed to stand at room temperature for 20 minutes and then filtered. The filtrate was evaporated to dryness and the white residue triturated with water and then recrystallised from water/dimethyl formamide to give 0.14 g. of 2-guanidino-4-[3-(3methylureido)phenyl]-thiazole nitrate, m.p. 195°–197° C. (decomp.).

EXAMPLE 35

To a solution of 2-guanidino-4-(3-thioureidophenyl)-thiazole (0.3 g.) in dimethylformamide (5 ml.) was added silver nitrate (0.34 g.) in water (3 ml.). The resulting dark suspension was allowed to stand at room temperature for 1 hour, filtered and the clear filtrate evaporated to dryness. The residue was triturated with water and filtered to give 0.14 g. of 2-guanidino-4-(3-cyanamidophenyl)thiazole nitrate, m.p.>300° C.

EXAMPLE 36

A mixture of 2-guanidino-4-(2-amino-5-bromophenyl)thiazole (0.10 g.) and methylisothiocyanate (0.06 g.) was stirred overnight in dimethylformamide (2 ml.). The crude reaction mixture was evaporated to dryness and the residual gum triturated with water. The solid was filtered off and air-dried to give 0.07 g. of 2-guanidino4-[2-bromo-5-(3-methylthioureido)phenyl]-thiazole, m.p. 135°–139° C.

The 2-guanidino-4-(2-amino-5-bromophenyl)thiazole used as starting material may be prepared as follows:

To a stirred solution of 2-bromo-5-nitroacetophenone (2.4 g.) and hydrogen bromide in glacial acetic acid (45% w/v, 6 drops) in chloroform (20 ml.) was added bromine (0.53 ml.) dropwise over a period of 10 minutes. The mixture was evaporated to dryness and the residual oil azeotroped with toluene. The crude oil was then dissolved in warm acetonitrile (10 ml.) and added to a boiling solution of amidinothiourea (1.18 g.) in alcohol (100 ml.). The mixture was boiled until the total volume was approximately 50 ml. and then allowed to cool to room temperature, whereupon the product, 2 guanidino4-(2-bromo-5-nitrophenyl)thiazole hydrobromide, was filtered off as light yellow crystals (3.2 g.), m.p. 270°–272° C.

To a boiling solution of 2-guanidino-4-(2-bromo-5-nitrophenyl)thiazole hydrobromide (0.63 g.) in acetic acid (30 ml.) and water (3.5 ml.) was added iron powder (0.85 g.). The mixture was stirred and then allowed to cool to room temperature. The mixture was then evaporated to dryness, and the residue azeotroped twice with toluene. The brown oily mixture was dissolved in methanol and 2 N sodium hydroxide added dropwise until the pH was just greater than 11. The mixture was filtered and the filtrate evaporated to about 5 ml., and the crude product, 2-guanidino-4-(2-amino5-bromophenyl)-thiazole was filtered off. This was recrystallised from ethyl acetate/petroleum ether (b.p. 40°–60° C.) to give the pure product (0.23 g.), m.p. 203°–5° C.

EXAMPLE 37

A mixture of 2-guanidino-4-(2-amino5-bromophenyl)thiazole (0.8 g.) and dimethyl (cyanoimido)dithiocarbonate (0.44 g.) was heated under reflux for 4 hours in methanol (5 ml). The reaction mixture was cooled to 0° C. and the solid which precipitated filtered off. Trituration of this solid with methanol gave 2-guanidino-4[2-bromo-5-(3-cyano-2-methylisothioureido)phenyl]-thiazole as a light brown solid which was dissolved in ethanolic methylamine (33% w/v, 3 ml.) and the solution allowed to stand at room temperature overnight. The clear solution was evaporated to dryness. The residue was purified by chromatography on silica using chloroform/methanol/concentrated aqueous ammonia 8:2:0.3 v/v/v to give 0.04 g. of 2-guanidino-4-[2-bromo5-(2-cyano-3-methylguanidino)-phenyl]thiazole as a gum which had the following n.m.r. in $d_6$ dimethyl sulphoxide: 2.8 (d,3H); 3.4 (s,$H_2O$); 7.0 (s,4H); 7.1 (s,1H); 7.2–7.9 (m,4H); 9.1 (s,1H).

EXAMPLE 38

A mixture of 1-[3-(2-guanidinothiazol-4-yl)phenylamino]-1-methylthio-2-nitroethylene (0.16 g.) and 2-[(5-dimethylaminomethylfuran-2-yl)methylthio]ethylamine (1 g.) was heated at 100° C. for 2 hours. The product was extracted 10 times with 5 ml. portions of diethyl ether and the residual gum was applied to Merck 60 F254 preparative plates and eluted with ethyl acetate/methanol/concentrated aqueous ammonia 6:1:1 v/v/v. The solid obtained (0.05 g.) was crystallised twice from acetonitrile to give 1-[3-(2-guanidinothiazol-4-yl)phenylamino]-1-[2-[(5-dimethylaminomethylfuran-2-yl)methylthio]ethylamino]-2-nitroethylene, m.p. 175°–180° C. (decomp.).

EXAMPLE 39

A mixture of 2-guanidino-4-(3-aminophenyl)thiazole (0.47 g.) and S-methyl-N-nitroisothiourea (0.3 g.) was heated under reflux overnight in methanol (5 ml.). The precipitated yellow solid was filtered off, washed with methanol and air-dried to give 0.4 g. of 2-guanidino-4[3-(2-nitroguanidino)phenyl]thiazole, m.p. 230°–235° C. (decomp.).

EXAMPLE 40

Reaction of 2-guanidino-4-(3-aminophenyl)-oxazole with methylisothiocyanate in dimethylformamide gave 2-guanidino-4-[3-(3-methylthioureido)phenyl]oxazole having the following n.m.r. in $d_6$DMSO: 2.8(d,4H); 3.25(s,$H_2O$); 6.9(s,4H); 7.2–7.7(m,5H); 7.8(s,1H); 9.5(s,1H).

The starting material may be obtained as follows:

Reaction of m-nitrophenacyl bromide with sodium acetate in ethanol gave m-nitrophenacyl alcohol. This was treated with dicyandiimide and HCl in aqueous methanol to give 2-guanidino4-(3-nitrophenyl)oxazole hydrochloride, m.p. 250°–251° C. The nitro residue was reduced with iron powder in acetic acid containing 10% v/v water to give 2-guanidino-4-(3-aminophenyl)oxazole.

We claim:

1. A guanidine derivative of the formula:

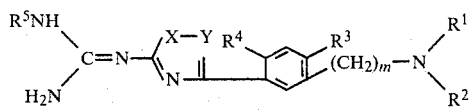

in which

X is sulphur:

Y is nitrogen, CH or CCH$_3$:

m is 0 or 1:

$R^1$ is hydrogen and $R^2$ is alkanoyl of 1 to 6 carbons or 4,5-dihydro-4-exothiazol-2-yl -A-B in which A is 3,4-dioxocyclobuten-1,2-diyl or C=Z in which Z is oxygen, sulphur, NCN, NNO$_2$, CHNO$_2$, NCONH$_2$, C(CN)$_2$, NCOR$^6$, NCO$_2$R$^6$, NSO$_2$R$^6$ or NR$^7$ in which R$^6$ is alkyl of 1 to 6 carbons and R$^7$ is hydrogen or alkyl of 1 to 6 carbons and B is alkyl, alkoxy or alkylthio of 1 to 6 carbons or NR$^8$R$^9$ in which R$^8$ and R$^9$, which may be the same or different, are hydrogen, alkyl of 1 to 10 carbons, alkenyl or alkynyl of 3 to 10 carbons in which the double or triple bond is separated from the nitrogen of NR$^8$R$^9$ by at least one carbon, (primary hydroxy-)alkyl of 2 to 6 carbons, alkoxyalkyl of 3 to 10 carbons in which the oxygen is separated from the nitrogen of NR$^8$R$^9$ by at least two carbons, or pyridylmethyl, or, when R$^9$ is hydrogen, R$^8$ is 2-[(5-dimethyl-aminomethylfuran-2-yl)methylthio]ethylamino, or R$^8$ and R$^9$ may be joined together to form a 5- or 6-membered non-aromatic ring which optionally contains an additional nitrogen or oxygen;

$R^3$ is hydrogen or fluorine;

$R^4$ is hydrogen or, when $R^3$ is hydrogen, $R^4$ is halogen or methyl:

$R^5$ is hydrogen, alkyl of 1 to 6 carbons or alkoxyalkyl of 3 to 10 carbons in which the oxygen atom is separated from the nitrogen atom of the guanidine residue by at least two carbons: and the pharmaceutically-acceptable acid-addition salts thereof.

2. A guanidine derivative as claimed in claim 1 in which -R$^2$ is -A-B in which A is 3,4-dioxocyclobuten-1,2-diyl or C=Z in which Z is oxygen, sulphur, NCN, NNO$_2$, CHNO$_2$ or NH and B is methyl, methoxy, methylthio, amino, methylamino, dimethylamino, n-propylamino, allylamino, propargylamino, 2-hydroxyethylamino, 2-methoxyethylamino, pyrid-2-ylmethylamino, 2-[(5-dimethylaminomethylfuran-2-yl)methylthio]ethylamino or morpholino, R$^4$ is hydrogen or, when R$^3$ is hydrogen R$^4$ is bromine, and R$^5$ is hydrogen, methyl or 2-methoxyethyl.

3. A guanidine as claimed in claim 1 in which Y is CH.

4. A guanidine derivative as claimed in claim 3 in which m is O, R$^3$ and R$^4$ are hydrogen and —R$^2$ is —A—B in which B is alkyl or NR$^8$R$^9$.

5. A guanidine derivative as claimed in claim 4 in which A is C=Z in which Z is oxygen or NCN, NNO$_2$, CHNO$_2$ or NH and R$^9$ is hydrogen.

6. A guanidine derivative as claimed in claim 5 in which R$^8$ is a hydrogen, methyl or propargyl.

7. The compounds 2-guanidino-4-(3-guanidinophenyl)thiazole, 2-guanidino-4-[3-(N$^2$-cyanoacetamidino)phenyl]thiazole, 2-[2-(2-methoxyethyl)guanidino]-4-[3-(2-cyano3-methylguanidino)-phenyl]thiazole, 2-guanidino4-[3-(2-cyano-3-propargylguanidino)phenyl]thiazole, 2-guanidino-4-[3-(3-methylureido)phenyl]thiazole and 2-guanidino-4-[3-(2-nitroguanidino)phenyl]-thiazole, and the pharmaceutically-acceptable acid-addition salts thereof.

8. The compounds 2-guanidino-4-[3-(2-cyano3-methylguanidino)phenyl]thiazole and 1-[3-(2-guanidinothiazol-4-yl)phenylamino]-1-methylamino2-nitroethylene, and the pharmaceutically-acceptable acid-addition salts thereof.

9. An antisecretory pharmaceutical composition comprising a guanidine derivative as claimed in claim 1 in association with a non-toxic pharmaceutically-acceptable diluent or carrier.

10. A method of inhibiting gastric secretion in a warm-blooded animal which comprises administering to the animal an effective amount of a compound of claim 1.

11. A guanidine derivative of the formula

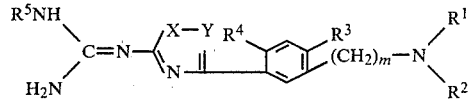

in which Y is nitrogen, CH or CCH$_3$, m is 0 or 1,

X is sulphur or oxygen, $R^1$ is hydrogen and $R^2$ is formyl, cyano, trifluoracetyl, acetyl, or 4,5dihydro-4-oxothiazol-2-yl or —R$^2$ is —A—B in which A is 3,4-dioxocyclobuten-1,2-diyl or C=Z in which Z is oxygen, sulphur, NCN, NNO$_2$, CHNO$_2$ or NH and B is methyl, methoxy, methylthio, amino, methylamino, dimethylamino, n-propylamino, allylamino, propargylamino, 2-hydroxyethylamino, 2-methoxyethylamino, pyrid-2-ylmethylamino, 2-[(5-dimethylaminomethylfuran-2-yl)methylthio]ethylamino or morpholino, or R$^1$ and R$^2$ are together imidazolidin-2-ylidene, R$^4$ is hydrogen or, when R$^3$ is hydrogen R$^4$ is bromine, and R$^5$ is hydrogen, methyl or 2-methoxyethyl, and the pharmaceutically-acceptable acid-addition salts thereof.

* * * * *